United States Patent [19]

Childs et al.

[11] Patent Number: 6,057,166

[45] Date of Patent: *May 2, 2000

[54] FECAL TEST METHOD

[75] Inventors: Mary Ann Childs, Baltimore; Anjana Prakash, Reisterstown; David Bernstein, Eldersburg, all of Md.

[73] Assignee: Universal Healthwatch, Inc., Columbia, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/577,623

[22] Filed: Dec. 22, 1995

[51] Int. Cl.$^7$ .................................................. G01N 33/533
[52] U.S. Cl. .............................. 436/525; 422/56; 422/61; 435/7.1; 435/7.92; 435/7.93; 435/7.94; 435/805; 435/810; 435/962; 435/970; 435/975; 436/518; 436/523; 436/525; 436/533; 436/808; 436/810; 436/811
[58] Field of Search ........................ 422/56, 61; 435/7.1, 435/7.92, 7.93, 7.94, 805, 810, 962, 970, 975; 436/518, 523, 525, 533, 808, 810, 811

[56] References Cited

U.S. PATENT DOCUMENTS

| | | | |
|---|---|---|---|
| 4,806,311 | 2/1989 | Greenquist | 422/56 |
| 4,859,612 | 8/1989 | Cole et al. | 436/523 |
| 5,011,770 | 4/1991 | Kung et al. | 435/6 |
| 5,094,956 | 3/1992 | Grow et al. | 436/66 |
| 5,141,850 | 8/1992 | Cole et al. | 436/525 |
| 5,198,365 | 3/1993 | Grow et al. | 436/66 |
| 5,270,166 | 12/1993 | Parsons et al. | 435/7.4 |
| 5,354,692 | 10/1994 | Yang et al. | 436/514 |
| 5,387,503 | 2/1995 | Selmer et al. | 435/5 |
| 5,395,754 | 3/1995 | Lambotte et al. | 435/607.4 |
| 5,460,785 | 10/1995 | Rhodes et al. | 424/1.49 |
| 5,518,887 | 5/1996 | Parsons et al. | 435/7.1 |
| 5,541,057 | 7/1996 | Bogart et al. | 435/5 |

FOREIGN PATENT DOCUMENTS

94/10571  5/1994  WIPO .

OTHER PUBLICATIONS

Webster's Dictionary, © 1984.
Millipore Catalogue, p. 84, 1982.
Millipore Catalogue, p. 19, 1991.
Hasan et al., FEMS Microbiology Letters, 120:143–148, 1994.
Hasan et al., Journal of Linical Microbiology, 33(11):2935–2939, 1995.
Parisi et al., Journal of Clinical Microbiology, 33(7):1963–1965, 1995.
Qadri et al., Journal of Linical Microbiology, 33(3):732–734, 1995.
Cholera Smart (TM) Package Insert, 1995.
J.A.K. Hasan et al., "Cholera DFA: An improved direct fluorescent monoclonal antibody staining kit for rapid detection and enumeration of *Vibrio cholerae* O1," FEMS Microbiology Letters, vol. 120, 1994, pp. 143–148.
J.A.K. Hasan et al, "Development and Testing of Monoclonal Antibody–Based Rapid Immunodiagnostic Test kits for Direct Detection of *Vibrio cholerae* O139 Synonym Bengal," Journal of Clinical Microbiology, vol. 33, No. 11, Nov. 1995; 2935–2939.
M. Parisi et al., "Evaluation of New Rapid Commercial Enzyme Immunoassay for Detection of Cryptosporidium Oocysts in Untreated Stool Specimens," Journal of Clinical Microbiology, vol. 33, No. 7, Jul. 1995; pp. 1963–1965.
F. Qadri et al., "Evaluation of the Monoclonal Antibody–Based Kit Bengal SMART for Rapid Detection of *Vibrio cholerae* O139 Synonym Bengal in Stool Samples," Journal of Clinical Microbiology, vol. 33, No. 3, Mar. 1995; pp. 732–734.
Vellacott et al., "An Immunofluorescent Test for Faecal Occult Blood", The Lancet, Jan. 3, 1981, pp. 18–19.
Julkunen et al., "Detection of Rotavirus in Faecal Specimens in Enzyme Immunoassay, Latex Agglutination and Electron Microscopy", Scand. J. Infect. Dis., 17:245–249, 1985.
Hasan et al., "A Novel Kit for Rapid Detection of *Vibrio cholerae* O1", Journal of Clinical Microbiology, vol. 32, No. 1, Jan. 1994, pp. 249–252.

*Primary Examiner*—James C. Housel
*Assistant Examiner*—Bao-Thuy L. Nguyen
*Attorney, Agent, or Firm*—Foley & Lardner

[57] ABSTRACT

A method is disclosed for determining the presence or amount of analyte in a fecal sample. The method comprises the steps of (A) contacting the fecal sample with an extraction reagent comprised of at least one detergent and at least one buffer to form a mixture, (B) applying the mixture to an absorbent filter that is in proximity to or in contact with an immunoassay such that analyte present in the sample is transferred to the immunoassay, and (C) detecting the presence of analyte by said immunoassay. In a preferred embodiment, the immunoassay comprises a porous strip containing immunoreagents for detecting analyte.

8 Claims, 5 Drawing Sheets

FECAL TEST METHOD

FIELD OF THE INVENTION

This invention relates to an improved method for analyzing fecal samples. In particular, this invention relates to a method for preparing fecal samples for immunoassays that does not require a separate sample pre-treatment step to remove interfering substances.

BACKGROUND OF THE INVENTION

Fecal, or stool samples are routinely tested for the presence of viruses, bacteria, parasites, other organisms, and antigens shed from such organisms. Methods for conducting such assays begin with stool collection, usually involve a number of fecal sample manipulation steps and typically end with the development of a signal such as color formation within a signal development means to indicate the presence or absence of a test analyte.

Stool collection is usually non-invasive and is ideal for obtaining samples of certain digestive disease organisms such as salmonella and cholera. Stool can be collected with a swab during examination and applied directly to a test surface or volume.

Traditional fecal examinations have used complex chemical and microbiological methods. These methods are being replaced with immunoassay methods. Immunoassay methods are highly sensitive and require only a small sample. Some immunoassay methods such as latex agglutination and enzyme immunoassays can be performed with test kits that contain vials and reagent solutions that are combined in a particular way to obtain a test result.

Although many immunoassay methods do not require electronic instrumentation or university trained clinicians for their use, they are not easily carried out in underdeveloped areas of the world where modern devices and techniques are poorly understood. Even the simplest immunoassays usually require timed addition of reagents to test samples and the manipulation of plastic test parts that have to be brought together in a proper order.

The application of immunoassay techniques to fecal analysis in particular is difficult for several reasons. Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician.

However, stool samples have to be processed before their use in an immunoassay in order to remove interferences. This processing can cause complexity within the test method and prevents more widespread use of cholera tests in rural and lesser developed regions where machinery and reagents for processing are nonexistent.

Any reduction in the number of steps required to perform a fecal test and any reduction in contact between test operator and the test material could be a boon to testing in this area, particularly where a lethal disease agent such as cholera is involved. Such an advance would directly advance health by allowing earlier and more complete testing of cholera.

Attempts have been made to alleviate the methodology problem of handling stool specimens. For example, M. A. Grow et al. in U.S. Pat. No. 5,198,365 describe a fecal sample handling method for a hemoglobin immunoassay that requires dilution of a stool specimen by 10 to 100 fold.

Although dilution possibly can simplify the assay procedure, it lowers sensitivity by a dilution factor. A 10 to 100 fold dilution step is particularly unacceptable for many tests of infectious agents such as cholera because greater test sensitivity is desired to detect these agents at earliest clinical time periods.

On the other hand, if a sample is tested without a significant dilution (i.e. more than 3 fold) then a centrifugation and/or filtering step is generally required as described by Vellacott et al., Lancet (Jan. 3, 1981) and by Jikunen et al. in the Scand. J. Infect. Dis. 17: 245 (1985).

A recent attempt to eliminate the complexity problem in testing stool specimens was described in J. Clin. Micro. 32: 249 (1994) by J. A. K. Hasan et al. This reference cites a rapid calorimetric immunodiagnostic kit for the detection of the presence of Vibrio cholera 01 in clinical specimens.

In the procedure a stool specimen is passed through a filter that is separate from other kit components. Four drops of the stool filtrate are added to two drops of reconstituted gold labeled anti-vibrio cholera antibody. A swab is first added to the solution and then placed in an immunoassay testing device. Within the device, formed immune complexes are captured on a porous membrane that contains immobilized anti-vibrio cholera antibody.

Unfortunately, the separate filtration step in this procedure prolongs the test. The test is too complex for many untrained people and requires separate manipulation of two vials, one vial cap, a swab and an immunoassay device. Furthermore, test kits and methods that require many manipulations have more sources of error which lead to higher error rates. Finally, manufacturing costs increase when multiple parts and separate reagents are added to test kits.

Thus, there exists a need for simpler and safer fecal test devices.

SUMMARY OF THE INVENTION

Accordingly, it is an object of the invention to eliminate or reduce the complexity of methods and kits for testing fecal samples.

A second object of the invention is to help limit spread of diseases present in fecal samples through the testing process itself.

Yet a third object of the invention is to provide a relatively inexpensive fecal sample test.

Yet another object of the invention is to provide a reliable fecal test that is relatively easier to use.

In accomplishing these and other objectives, one aspect of this invention provides a method for detecting analyte in a fecal sample. The method comprises the steps of: A) contacting a fecal sample with an extraction reagent comprised of at least one detergent and at least one buffer to form a mixture; B) applying the mixture to an absorbent filter that is in proximity to or in contact with a immunoassay such that analyte present in the sample is transferred to the immunoassay; and C) detecting the presence of analyte in the immunoassay.

In one preferred embodiment of the method, the immunoassay comprises a porous strip that comprises a) a first group of particles having bound thereto a binding component capable of specifically recognizing an analyte; and b) a second group of particles having bound thereto a binding component capable of specifically recognizing said analyte, wherein the average diameter of the particles in the first group is larger than the average diameter of the particles in the second group.

Particularly preferred is an embodiment wherein the larger particles are comprised of selenium and the smaller particles are comprised of gold.

The invention also provides a test kit for detection of analyte comprised of: A) an extraction reagent comprised of at least one detergent and at least one buffer; B) an absorbent filter that is in proximity to or in contact with a chromatographic immunoassay strip comprising immunoreagents for detecting analyte present in the sample.

In one preferred embodiment of the kit, the chromatographic strip comprises: A) gold particles coated with antibody against the analyte; and B) antibody against the analyte immobilized within a region of the strip.

The methods and kits of the present invention eliminate or reduce much of the complexity associated with prior art assay methods and, as a result, simplify operator training requirements and lower the cost of detecting analyte present in fecal samples. Furthermore, they help protect the test user from infection by accidental contact with fecal samples and treated fecal samples.

These advantages are made possible by simplifying the fecal test itself. In the inventive assay, the sample extraction step employs a fecal filter that is part of the immunoassay itself. This combination eliminates one or more tedious sample preparation and assay manipulation steps present in other tests.

As a result of these changes the fecal assay is easier to carry out and fewer part are needed in the diagnostic kit. For example, only one sample container (e.g., a tube) need to be used for sample extraction. Further, a separate membrane filter tube, filter cap, and centrifugation step are not required. Furthermore, no additional fluid addition step such as a wash step is required.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
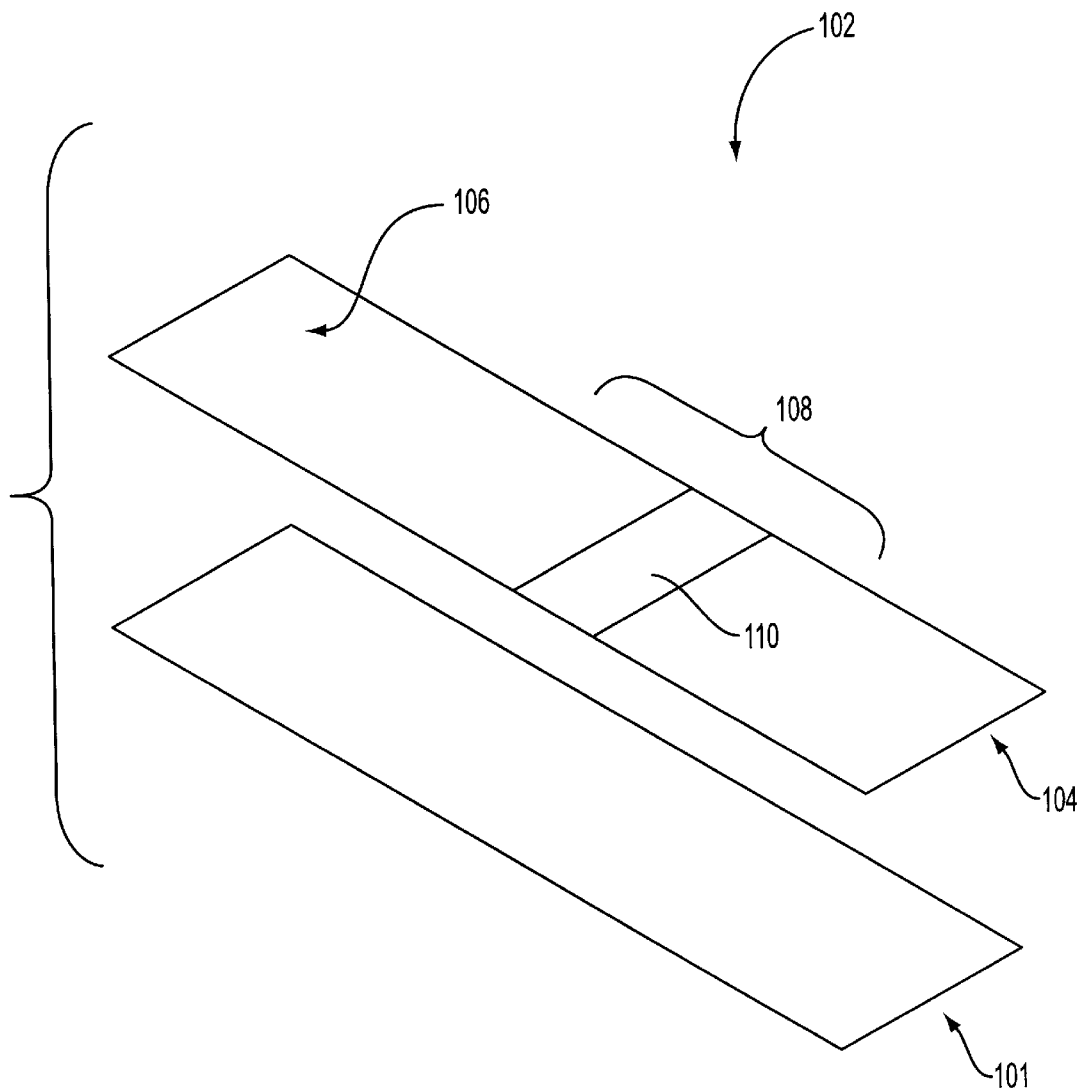
FIG. 1 is an exploded view of one embodiment of the device in accordance with this invention.

The present inventors surprisingly discovered that a fecal sample test could be simplified by combining an immunoassay with a fecal filtering device. Moreover, the present inventors discovered that, when a suitable extraction reagent was used to contact a fecal sample, interfering substances and debris were retarded on the filter. As a result, additional sample preparation an manipulation steps were eliminated.

As used for the detection of analyte from stool samples, the method of this invention comprises the steps of: 1) contacting a fecal sample that is suspected of containing analyte with an extraction reagent to form a mixture; 2) applying the mixture to an absorbent filter that is in proximity to or in contact with an immunoassay such that analyte present in the sample is transferred to the immunoassay; and 3) detecting the presence of analyte by the immunoassay, for example, by development of color in the assay.

In a preferred embodiment, a single absorbent filter serves both to filter the fecal sample and provide a support for the immunoassay. In this case, the porosity of the absorbent filter can be chosen based on optimal separation of test analyte from interfering fecal substances during operation of the device. Porous plastic, plastic membrane, glass fiber and the like are suitable for the absorbent filter. For example, where fiber filters are used, the particle retention size of the filter can be chosen to be between 0.1 um and 20 um and preferably between 0.4 um and 5 um. Skilled artisans readily will be able to determine acceptable filters for these purposes.

In another preferred embodiment, the absorbent filter is in proximity to, or attached to a separate porous strip for the immunoassay. The extracted analyte then passes through the filter into the immunoassay strip. The type of absorbent filter is chosen based on how well it separates fecal matter from analyte.

Other combinations of immunoassays and absorbent filter are possible and readily will be recognized by skilled artisans.

The extraction reagent is any reagent that can extract analyte from the fecal sample. Acceptable extraction reagents comprise an aqueous fluid comprising at least one buffer and at least one detergent. Acceptable buffers can be in a concentration between 1 mM and 1 M and more preferably in a concentration of between 5 mM and 250 mM, and will have a pH between 3 and 13 and more preferably between 6 and 9. The buffer composition can be one or more chemical compounds which are known to skilled artisans. Advantageously, the volume of extraction reagent used will be at least about the same volume as the fecal sample.

The detergent generally is an amphoteric compound, and many such detergents are known to skilled artisans. Examples of detergents include: deoxycholate, Tween-20, triton X-100, and sodium docedyl sulfate. Generally, the detergent will be in a concentration between its critical micelle concentration and 10% wgt/vol. The critical micelle concentration of a detergent is defined as the concentration above which the detergent molecules self associate to form micelles. In the case where the detergent comprises at least one chemical group that dissociates near neutral pH (pka between pH 5 and 9) the buffer and detergent may be the same substance.

An immunoassay suitable for the present invention will detect analyte from an aqueous sample that contacts it. Conveniently, detection can be carried out by the formation or disappearance of color from at least one part of the assay. Many other possibilities, however, will readily be recognized by skilled artisans.

A preferred immunoassay is an immunochromatographic strip assay which may be conveniently combined with the absorbent filter that filters the extracted fecal sample. In a preferred embodiment, the immunochromatographic strip assay comprises: a) gold particles coated with antibody against analyte; and b) antibody against analyte immobilized within a region of the strip. The antibody-labelled gold particles are preferably dried on or within the chromatographic strip during its manufacture.

During operation of the one method embodiment in accordance with this invention, a fecal specimen reacts with the extraction reagent to release analyte (if present) into a small quantity of fluid (preferably 10 ul to 250 ul in volume) within a water impermeable container. A strip that comprises an absorbent filter and a strip detection means is placed into the container or already is present therein. Fluid containing antigen (if present) then wicks into the strip. The absorbent filter traps debris and solids while extracted antigen continues to diffuse into the strip with the liquid. The filtered extraction fluid which contains extracted antigen re-suspends antibody labelled particles that are present in the strip detection means. Immune complexes form between antibody-labelled particles and antigens. These immune complexes diffuse through interstices of the strip detection means, including a region which comprises immobilized antibody against the analyte. Some of the immobilized antibodies capture analyte that is bound to particles, and the capture of particles can be detected visually.

The use of gold particles in the immunoassay is a preferred embodiment because the particles can be seen directly without the need, for example, of a chromogenic enzyme reaction which can be employed in immunoassays in accordance with this invention. In the case of gold particles, the presence of analyte in the fecal sample is detected by the formation of a red to purple region within the region of the strip that contains immobilized antibody. If no analyte is present, then no color is detected.

Advantageous devices and methods for performing particle assisted assays and fecal sample assays are provided in co-pending application Ser. Nos. 08/577,108 and 08/577,128, (now U.S. Pat. No. 5,766,962) both filed Dec. 22, 1995 and which are herein expressly incorporated by reference in their entireties.

Referring now to the Figures, five physical embodiments in accordance with the present invention are provided.

FIG. 1 depicts one embodiment of a device 102 in accordance with this invention. In this embodiment the absorbent filter and the immunoassay exist as a single unit, comprised of upper strip 104 and mylar backing 101. In this embodiment, portion 106 serves to filter the extraction fluid and fecal sample mixture. Immunoassay portion 108 comprises reagents for detecting analyte. Antibody is directly and/or indirectly immobilized in region 110. Upper strip 104 is attached to mylar backing 101 throughout its lower surface.

During operation, device 102 is placed into, or is already present in a container such as a test tube that contains an extraction fluid and fecal sample mixture. The device 102 is positioned such that portion 106 of unit 104 contacts the mixture. The mixture enters portion 106 and filtered material passes through this portion to enter portion 108. Detection of analyte is completed by the formation of color in region 110 in response to the presence of analyte.

Figure 2:
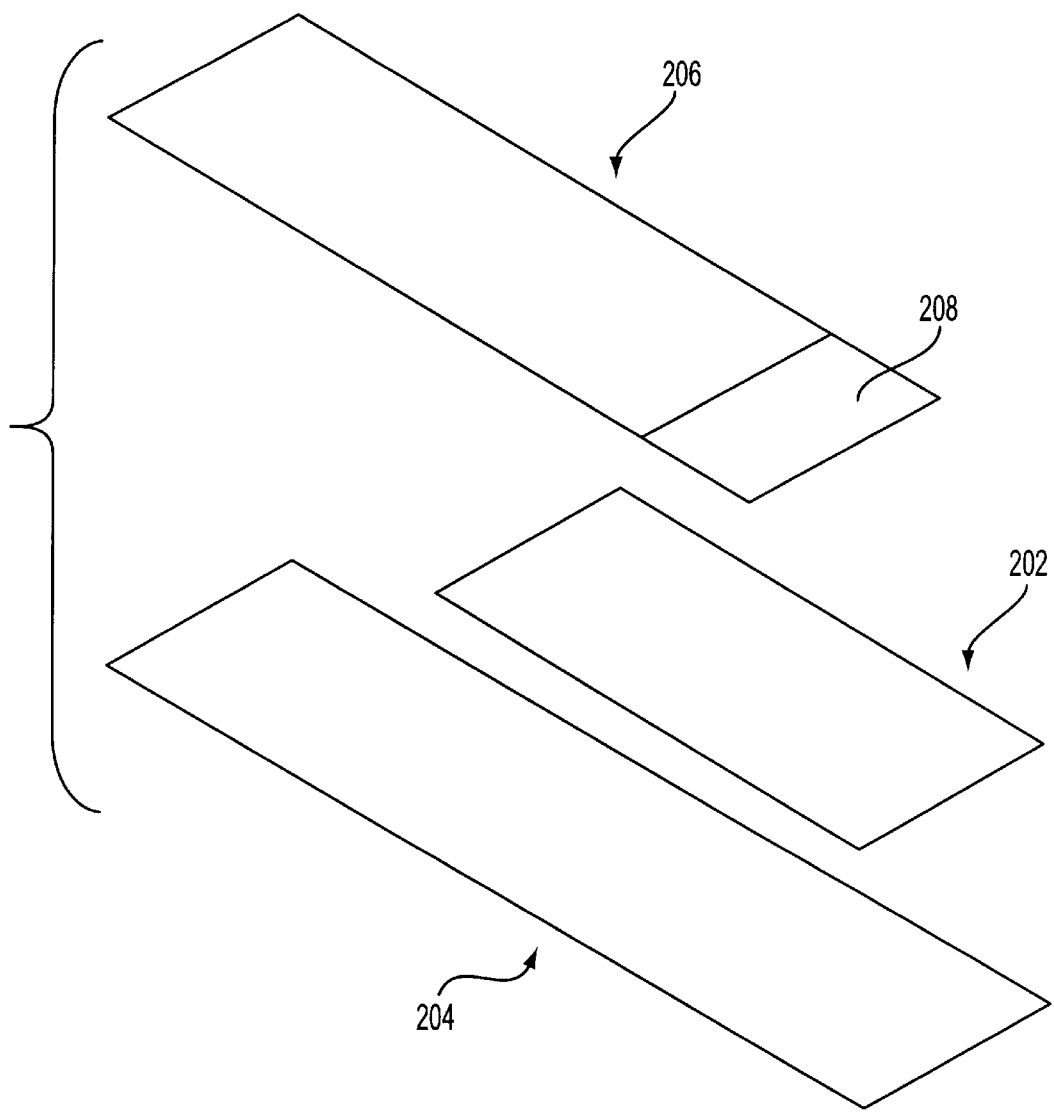
FIG. 2 is an exploded view of another embodiment of the device in accordance with this invention.

FIG. 2 depicts a variation of the device of FIG. 1 in which absorbent pad 202 is interposed between mylar backing strip 204 and immunoassay portion 206 comprising region 208 that contains, inter alia, immobilized antibody. In this embodiment, immunoassay portion 206 is affixed to mylar backing 204 along its lower surface except for the portion that overlies absorbent pad 202. Absorbent pad 202 is affixed to mylar backing 204 along its entire lower surface.

The device of FIG. 2 operates the same way as the device of FIG. 1, except that absorbent pad 202 pulls aqueous fluid up the strip and through (from the top surface to the bottom surface) the region that comprises immobilized antibody.

Figure 3:
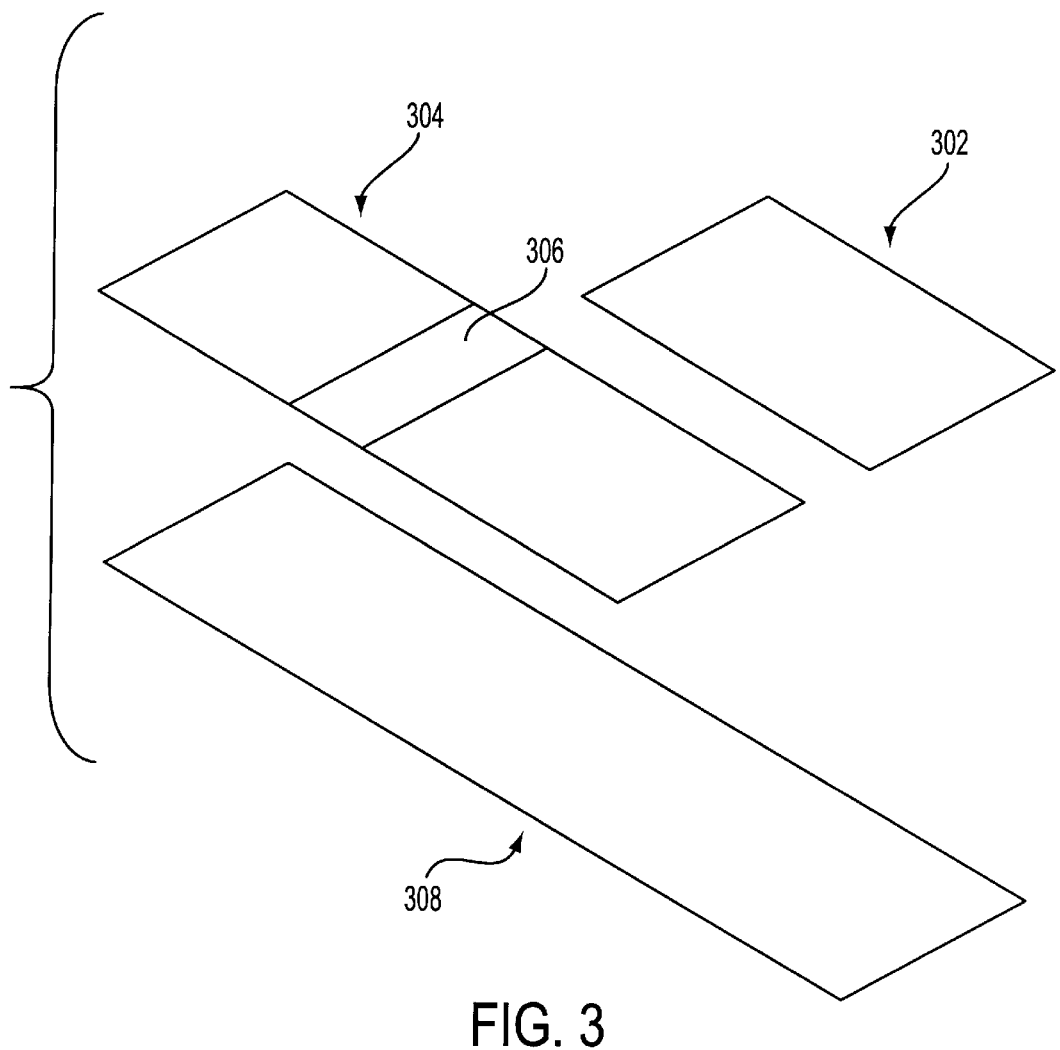
FIG. 3 is an exploded view of another embodiment of the device in accordance with this invention.

FIG. 3 depicts another variation of the FIG. 1 device in which absorbent pad 302 is present above and in proximity to or in contact with a separate chromatographic immunoassay strip 304 comprising region 306 that contains, inter alia, immobilized antibody. In this embodiment, absorbent pad 302 is affixed to mylar backing 308 except for the portion that overlies the immunoassay strip 304. Immunoassay strip 304 is affixed to mylar backing 308 along its entire length.

The device of FIG. 3 operates the same way as the device of FIG. 1, except that absorbent pad 302 pulls aqueous fluid up the strip and up through (along the axis of the membrane surface) the region that comprises immobilized antibody.

Figure 4:
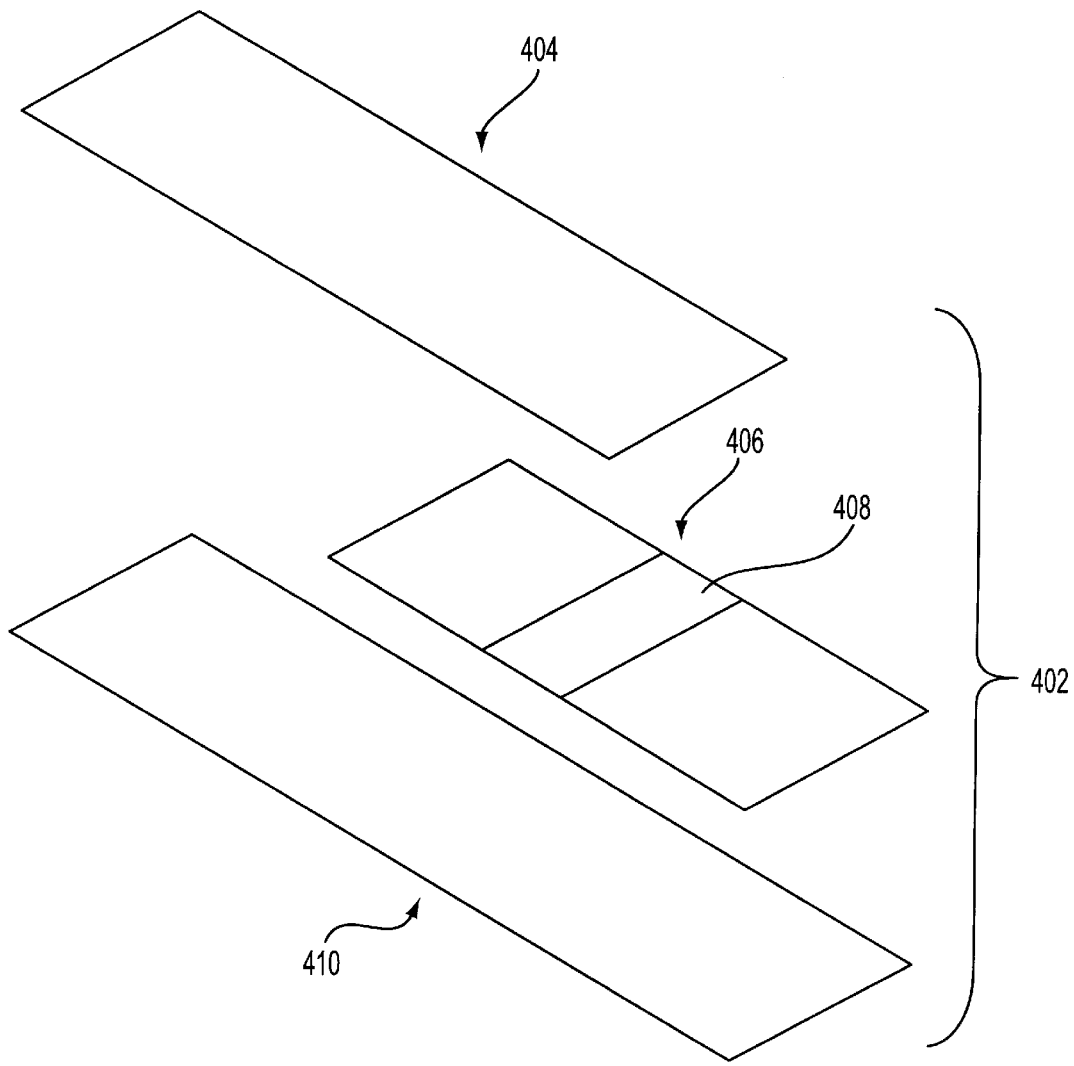
FIG. 4 is an exploded view of another embodiment of the device in accordance with this invention.

FIG. 4 depicts another device 402 comprised of absorbent filter 404 that physically contacts immunoassay strip 406. The immunoassay strip 406 comprises reagents for detecting analyte. The immobilized antibody reagent is present in region 408. Strip 406 is affixed to mylar backing 410 along its entire lower surface. Absorbent filter 404 is affixed to mylar backing 410 along its lower surface except for that part which overlies and contacts strip 406.

During operation, device 402 is present in or placed into a test tube that contains an extraction fluid and fecal sample mixture. The mixture enters absorbent filter 404 and filtered fluid then enters strip 406. Detection of analyte is completed by the formation of color in region 408 in response to the presence of analyte.

Figure 5:
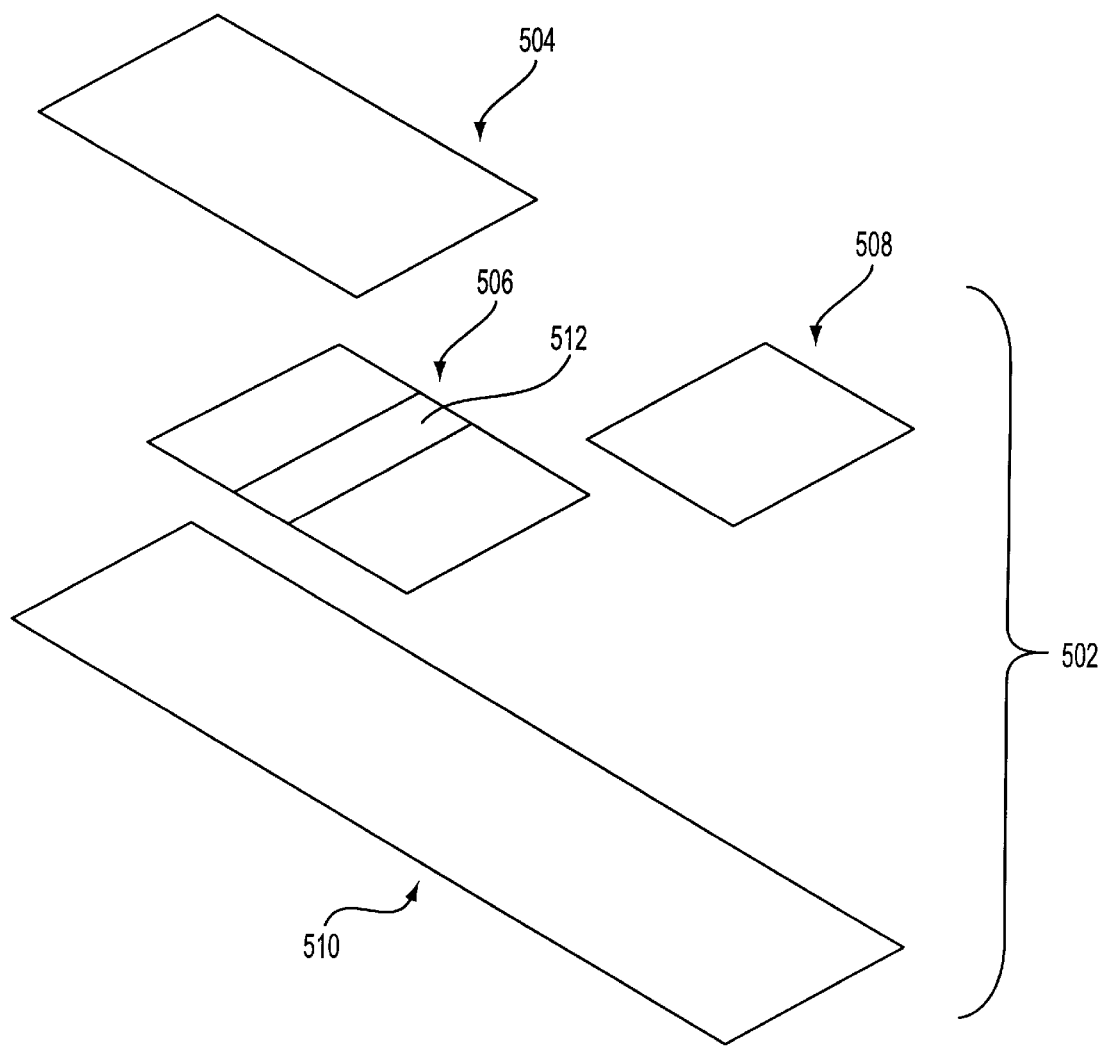
FIG. 5 is an exploded view of another embodiment of the device in accordance with this invention.

FIG. 5 depicts device 502 which comprises absorbent filter 504, immunoassay strip 506 and absorbent pad 508, which are affixed to mylar backing 510. The ends of absorbent filter 504 and absorbent pad 508 that protrude towards the middle of the device can overlap on top of strip 506 or, alternatively, can abut the ends of strip 506. Absorbent filter 504, strip 506 and absorbent pad 508 are affixed to mylar backing 510.

In this preferred embodiment, absorbent filter 504 filters the extraction fluid and fecal sample mixture. Strip 506 comprises reagents for detecting analyte. The immobilized antibody reagent is present in region 512.

During operation, device 502 is present in or placed into a test tube that contains an extraction fluid and fecal sample mixture such that portion 504 contacts the mixture. The mixture enters portion 504 and filtered material passes through this portion to enter strip 506. Absorbent pad 508 draws aqueous fluid up the strip and up through (along the axis of the membrane surface) the region that comprises immobilized antibody. Detection of analyte is completed by the formation of color within region 512 in response to the presence of analyte.

The following example is presented by way of illustration and not by way of limitation.

EXAMPLE

Preparation of particles: One hundred milliliters of a 0.03% w/v selenium dioxide solution were heated to boiling. Then, 2.25 milliliters of a freshly prepared solution of 2% ascorbic acid were added to the 0.03% $SeO_2$ solution. The admixture was boiled until its volume evaporated to 50 milliliters and cooled to room temperature. The optical density of the cooled solution at 520 nm and 580 nm was 1.457 and 1.167 respectively. The colloidal selenium that was prepared by this treatment was centrifuged at 10000×g for 15 minutes. The supernatant was discarded and the pellet was re-suspended in 100 ml of distilled water.

A 4% solution of gold chloride was prepared by dissolving 360 mg of gold chloride (tetrachloroauric acid trihydrate) into 9 milliliters of deionized water. A 1% solution of sodium citrate was prepared by dissolving 1.0 gram of sodium citrate into 100 milliliters of deionized water. Three liters of deionized water were placed into a 4 liter beaker and brought to a boil on a hot plate. Then 7.5 milliliters of the 4% gold chloride solution were added to the boiling water. Seventy two milliliters of the 1% sodium citrate solution were added to the beaker and the solution was boiled until its volume was reduced to 2.2 liters. A colloidal gold solution was removed from the hot plate and allowed to cool to room temperature. The cooled colloidal gold solution was filtered through a 0.2 micron cellulose acetate filter unit into a clean amber bottle. Optical densities at 520 nm and 580 nm of the resultant filtrate were 1.54 and 0.455 respectively.

A one milliliter aliquot of colloidal selenium was mixed with an equal volume of colloidal gold. The pH of this mixture was 5.0. The combined selenium-gold mixture was centrifuged at 10000×g for 1 minute to remove any aggregated material. The pH of the supernatant was adjusted to 8.0 by the careful addition of 0.2 M potassium carbonate.

Preparation of mouse monoclonal Vibrio cholera antibody: Purified Vibrio cholera antibody was commercially obtained from Global Diagnostics, Gainesville, Fla. The antibody was dialyzed against 0.002 M borax buffer pH 8.2, filtered through a 0.2 micron cellulose acetate filter, and diluted in the same buffer to a final concentration of 100 ug per milliliter.

Labelling of selenium-gold mixture with antibody The colloidal selenium and colloidal gold solutions were mixed in a 50/50 volume to volume ratio. The pH of the mixture was adjusted to 8.0 with 0.2 M potassium carbonate. Two hundred microliters of the anti vibrio cholera monoclonal antibody (100 ug/ml) were added to 2.0 milliliters aliquots of the colloidal selenium-colloidal gold mixture. Then 200 microliters of 20% bovine serum albumen were added to each aliquot. Each mixture was incubated for 5 minutes at room temperature. The antibody treated mixtures were centrifuged at 16,000×g for 5 minutes. The supernatants were removed and each pellet was re-suspended in 0.02 M Tris buffer pH 8.2 containing 1% bovine serum albumin. Each preparation was washed twice. After the last wash the pellet was re-suspended in 100 microliters of 0.02 M Tris buffer pH 8.2 containing 1% bovine serum albumin.

Application of antibody to nitrocellulose strips Mylar backed five micron nitrocellulose (Gelman Sciences, Ann Arbor, Mich.) was cut into 22 mm×4 mm strips. Rabbit anti-vibrio cholera affinity purified antibody (Louisiana State University, Baton Rouge) was diluted in 0.05 M sodium borate buffer pH 8.2 to a concentration of 1.6 mg/ml. One and one half microliters of antibody were spotted near the center of the nitrocellulose strip. The strips were dried in a vacuum desiccator.

A vinyl strip with acrylic adhesive was cut into 4 mm×70 mm portions. The prepared mylar backed nitrocellulose strips were affixed onto these cut vinyl strips. One absorbent paper cut to 4 mm×30 mm (Type III, Gelman Sciences) was affixed to overlap the top of each nitrocellulose strip and one glass fiber pad (Gelman Sciences) was affixed to overlap the bottom of each nitrocellulose strip. Ten microliters of the selenium-gold antibody mixture were pipetted onto each glass fiber pad and dried in a desiccator at room temperature overnight.

Preparation of Extraction buffer Extraction buffer was prepared by adding 1% Triton X-100 (vol/vol) and 1% bovine serum albumin (wgt/vol) to 0.02 M Tris buffered saline at pH 8.0.

Testing of selenium-gold antibody conjugates Vibrio cholera 01 (ATCC strain #11628) and Vibrio cholera non 01 (ATCC strain #14547) were grown in alkaline peptone water overnight at 35 degrees C. An aliquot of each sample was centrifuged at 5000×g for ten minutes. The supernatants were removed and each pellet was re-suspended in a saline solution to an optical density at 650 nm of 0.040 (approximately $10^8$ organisms per milliliter).

Fifty microliters of each sample were pipetted into 10 mm×75 mm test tubes. One hundred microliters of extraction buffer were added to each tube. A test strip was placed in each tube such that fluid diffused up and through each nitrocellulose strip. After 10 minutes each strip was examined for the presence of color in the region where antibody had been immobilized. The results were as follows:

| ATCC #11628 Vibrio cholera 01 | | | | ATCC #14547 Vibrio cholera non01 | | |
|---|---|---|---|---|---|---|
| $10^8$ | $10^7$ | $10^6$ | $10^5$ | $10^8$ | $10^7$ | $10^6$ |
| 3+ | 2+ | 1+ | N | N | N | N |

4+ very strong color development
3+ strong color development
2+ moderate color development
2+ weak color development
N no reaction Stool specimens were obtained from the Hospital San Juan de Dios by the Ministerio de Salud Pubicay Asistencia Social, Direccion General de Services de Salud, Guatamala City, Guatamala Calif. Each sample was cultured as follows: 10 ul added to 10 ml of alkaline peptone broth and incubated at 30 degrees C. overnight. A sample of each broth was then subcultured onto TCBS (thiosulfate, citrate, bile salts and sucrose) agar selective media and incubated at 37 degrees C. for 18 hrs.

Stool samples were tested using the prepared test strips. Fifty microliters of each sample were pipetted into 10 mm×75 mm test tubes. One hundred microliters of extraction buffer were added to each tube. A test strip was placed in each tube such that fluid diffused up and through each nitrocellulose strip. After 10 minutes each strip was examined for the presence of color in the region where antibody had been immobilized.

Control tests were performed on the same stool samples using a commercially available cholera test SMART lot 120 (New Horizons Diagnostics Corp. Columbia, Md.) according to the manufacturer's package insert.

| | Test results were | | |
|---|---|---|---|
| SAMPLE | DESCRIPTION | STRIP | CONTROL |
| TCBS CULTURE POSITIVE FECAL SAMPLES | | | |
| J.G. | liquid | pos | pos |
| D.H. | clear | pos | neg |
| TCBS CULTURE NEGATIVE FECAL SAMPLES | | | |
| M.M. | liquid | neg | neg |
| R.M. | liquid | neg | neg |
| O.R. | semi liquid | neg | neg |
| A.G. | brown, semi liquid | neg | neg |

In each test, the strip assay result agreed with the culture assay results.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A method for determining the presence or amount of analyte in an unfiltered fecal sample comprising the steps of:
   A. contacting said fecal sample with an extraction reagent comprising at least one detergent at a concentration of at least its critical micelle concentration to form a mixture comprising fecal matter and fluid containing antigen, said antigen comprising at least some of said analyte from said fecal sample;
   B. separating said fecal matter from said fluid containing antigen by wicking the mixture of step A into a test strip, wherein said test strip comprises absorbent material that contains immunoassay reagents, said absorbent material further comprising a fibrous filter that contacts said liquid and collects said fecal matter; and
   C. detecting the presence of analyte from a signal produced by said test strip.

2. The method of claim 1, wherein said fibrous filter is selected from the group consisting of glass fiber and cellulose paper.

3. The method of claim 2, wherein said fibrous filter is further characterized as having an effective porosity of 5.0 microns.

4. The method of claim 1, wherein step C comprises detecting a color produced within said strip.

5. The method of claim 1, wherein said fecal sample is contacted with at least an equal volume of extraction reagent.

6. The method of claim 1, wherein said detergent is selected from the group consisting of deoxycholate, polyoxyethylene-sorbitan monolaurate, t-octylphenoxypolyethoxyethanol and sodium dodecyl sulfate.

7. The method of claim 1, wherein said reagents necessary to conduct an immunoassay comprises (i) a first group of selenium particles having bound thereto a binding component capable of specifically recognizing analyte, and (ii) a second group of gold particles having bound thereto a binding component capable of specifically recognizing said analyte, wherein the average diameter of said selenium particles in said first group is larger than the average diameter of said gold particles in said second group.

8. A method for determining the presence or amount of analyte in an unfiltered fecal sample comprising the steps of:
   A. contacting said fecal sample with an extraction reagent comprising at least one detergent at a concentration of at least its critical micelle concentration to form a mixture comprising fecal matter and fluid containing antigen, said antigen comprising at least some of said analyte from said fecal sample;
   B. separating said fecal matter from said fluid containing antigen by wicking the mixture of step A into a test strip, wherein said test strip comprises absorbent material that contains at least one immunoassay reagent, said absorbent material further comprising a filter that contacts said liquid and collects said fecal matter; and
   C. detecting the presence of analyte from a signal produced by said test strip.

* * * * *